United States Patent
Davidai

(10) Patent No.: US 8,618,148 B2
(45) Date of Patent: Dec. 31, 2013

(54) USE OF TELMISARTAN FOR THE PREVENTION AND TREATMENT OF VASCULAR HEADACHE

(75) Inventor: Giora Davidai, New Canaan, CT (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 1972 days.

(21) Appl. No.: 11/454,720

(22) Filed: Jun. 16, 2006

(65) Prior Publication Data

US 2006/0234946 A1 Oct. 19, 2006

Related U.S. Application Data

(63) Continuation of application No. 10/925,788, filed on Aug. 24, 2004, now abandoned.

(60) Provisional application No. 60/500,817, filed on Sep. 5, 2003.

(51) Int. Cl.
*A01N 43/50* (2006.01)
*A01N 43/52* (2006.01)
*A61K 31/415* (2006.01)

(52) U.S. Cl.
USPC ............................ 514/385; 514/394; 514/395

(58) Field of Classification Search
USPC .................... 514/190, 385, 394, 395
See application file for complete search history.

(56) References Cited

U.S. PATENT DOCUMENTS 5,977,145 A * 11/1999 Silberstein et al. ........... 514/338

FOREIGN PATENT DOCUMENTS

| CA | 2436361 A1 | 8/2002 |
| WO | WO 00/02543 | 1/2000 |

OTHER PUBLICATIONS

Erling Tronvik et al; Prophylactic Treatment of Migraine with an Angiotensin II Receptor Blocker; Jama, Jan. 1, 2003 vol. 289 No. 1 pp. 65-69; American Medical Association.
Mahyar Etminan et al; Efficacy of Angiotensin II Receptor Antagonists in Preventing Headache: A Systematic Overview and Meta-analysis; American Journal of Medicine, Jun. 1, 2002 vol. 112 No. 8 pp. 642-646; Excerpta Medica, Inc.
Telmisartan BIBR 277, Micardis, Pritor; Drugs in R&D (2002) vol. 3 No. 4 pp. 250-256; Adis International Limited; XP001182726, ISSN: 1174-5886.
International Search Report Reference No. PCT/EP2004/009709.

* cited by examiner

*Primary Examiner* — Yong Chong
(74) *Attorney, Agent, or Firm* — Michael P. Morris; Timothy X. Witkowski; Usha R. Patel

(57) ABSTRACT

The present invention relates to a method for the prophylaxis of vascular headaches which do not originate from hypertension, especially migraine, the method comprising administration of telmisartan to a subject in need of such a treatment. The present invention relates also to a method for the prophylaxis of vascular headaches, comprising the co-administration of telmisartan in combination with other drugs suitable for migraine prophylaxis and/or acute treatment of migraine.

7 Claims, No Drawings

USE OF TELMISARTAN FOR THE PREVENTION AND TREATMENT OF VASCULAR HEADACHE

RELATED APPLICATIONS

This application claims priority benefit of U.S. Ser. No. 60/500,817, filed Sep. 5, 2003, which is hereby incorporated by reference in its entirety.

FIELD OF THE INVENTION

The present invention relates to a method for the prophylaxis of vascular headaches which do not originate from hypertension, especially migraine, the method comprising administration of {4'-[2-n-propyl-4-methyl-6-(1-methylbenzimidazol-2-yl)benzimidazol-1-ylmethyl]biphenyl-2-carboxylic acid} (telmisartan) to a subject in need of such a treatment. The present invention relates also to a method for the prophylaxis of vascular headaches, comprising the co-administration of telmisartan in combination with other drugs suitable for migraine prophylaxis and/or acute treatment of migraine.

The invention further relates to suitable pharmaceutical compositions comprising telmisartan and at least one other drug used in migraine prophylaxis, as a combined preparation for simultaneous, separate or sequential use in the prophylaxis of said disease. The invention relates further to the use of telmisartan, optionally in combination with said other antimigraine drugs for the manufacture of a pharmaceutical composition for the prophylaxis of vascular headaches.

BACKGROUND OF THE INVENTION

Migraine is one of the most common neurological disorders, involving periodical attacks of headache and nausea as well as a plethora of other symptoms. Approximately 240 million people worldwide have an estimated 1.4 billion attacks of migraine each year (Tronvik, E. et al., JAMA, 1, 2003, pp. 65-69). Although considerable progress has been made, the pathophysiology of migraine is still not understood. It is a disorder that exhibits a spectrum of treatment responses in afflicted individuals. Although some of the patients can be cured with life style modification (trigger elimination) and can be treated with over-the-counter medications or by acupuncture, hypnosis and the like, the majority of the patients are in the need of prescription drugs for relief from the migraine and prevention of further attacks. The symptoms most in need of treatment are the head pain and gastrointestinal symptoms. But also photophobia and the aura have to be treated. The latter may also be quite disturbing and require treatment although its duration is relatively brief.

The exact pathogenesis of migraine is still unknown. In recent years a consensus has been emerging that in migraine both vascular and neural components are relevant and most probably interrelated.

Common drugs, which at present are used for the treatment of migraine and other forms of vascular headaches, are e.g. ergotamine, aspirin and NSAIDS. The gold standard of acute migraine treatment are the "triptans", e.g. sumatriptan and zolmitriptan. These triptans elicit their antimigraine effects due to their vasoconstrictive properties and presumably their inhibition of the release of the neuropeptide calcitonin gene related peptide (CGRP).

A completely novel approach to treat migraine is the use of CGRP antagonists (Doods, H. et al., Br. J. Pharmacol., 129, 2000, pp. 420-423). Such CGRP antagonists have been disclosed, for example, in WO 98/11128. In WO 03/015787 a CGRP antagonist has been disclosed, namely 1-[N²-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine, which is, in combination with a 5-HT$_{1B/1D}$ agonist or an ergot alkaloid, especially useful for the prevention and/or treatment of migraine.

Recently, in WO 01/97807 angiotensin II (AT II) type I receptor antagonists have been disclosed for the prevention and/or therapeutic treatment of patients suffering from vascular headache conditions and more particularly migraine. These compounds are known to interfere with the renin-angiotensin system (RAS) and have been used so long to treat common cardiovascular diseases, particularly arterial hypertension and congestive heart failure.

Tronvik et al. disclosed results of a randomized, double blind, placebo-controlled crossover study with an angiotensin II (AT II) type I receptor antagonist (candesartan), of patients suffering from migraine. The authors concluded that candesartan provided effective migraine prophylaxis with a good tolerability profile (JAMA, 1, 2003, pp. 65-69).

Hansson et al. published results from a double-blind, placebo-controlled study with irbesartan of patients having mild/moderate hypertension. The use of an AT II type I receptor antagonist seems to be associated with a significant reduction in the incidence of headache commonly seen in hypertensive patients (Arch. Intern. Med. 160, 2000, pp. 1654-1658).

Etminan et al. published data of a meta-analysis of 27 studies involving 12110 patients treated for hypertension. The authors came to the conclusion that the risk of headaches was about one third lower in patients taking an AT II receptor antagonist than in those taking placebo (Am. J. Med. 112, 2002, pp. 642-646).

SUMMARY OF THE INVENTION

It has been found that a particular member of the group of AT II type I receptor antagonists, namely telmisartan, provides unexpected advantages in the prophylaxis of vascular headaches, especially migraine, to a subject in need of such treatment, with high efficacy, independently of its known blood pressure reducing activity. INN Telmisartan, {4'-[2-n-propyl-4-methyl-6-(1-methylbenzimidazol-2-yl)benzimidazol-1-ylmethyl]biphenyl-2-carboxylic acid}, has been developed for the treatment of hypertension and other medical indications as disclosed in EP 0 502 314 B1 and U.S. Pat. No. 5,591,762 and is already sold on the market under the trade name Micardis®. It exists in two polymorphic forms as disclosed in WO 00/43370, U.S. Pat. No. 6,358,986 and U.S. Pat. No. 6,410,742. Sodium salts of telmisartan and its solvate, hydrate, and hemihydrate are disclosed in WO 03/037876.

A first aspect of the present invention relates to a method for the prophylaxis of vascular headache conditions not originating from hypertension, especially migraine, comprising administering a therapeutically effective amount of telmisartan, preferably alone, or in combination with a therapeutically effective amount of an other drug suitable for the prophylaxis of migraine to a subject in need of such treatment.

The second aspect of the present invention relates to a pharmaceutical composition for preventing a vascular headache condition not originating from hypertension comprising a therapeutically effective amount of telmisartan. Additionally it relates to a pharmaceutical composition of telmisartan in combination with a therapeutically effective amount of at least one other drug suitable for migraine prevention as a combined preparation for simultaneous or sequential administration.

Another embodiment of the present invention is the use of telmisartan, preferably alone, but also in combination with at least one other drug suitable for migraine prevention, for the manufacture of a pharmaceutical composition for prophylaxis of vascular headache which do not originate from hypertension, preferably migraine.

DETAILED DESCRIPTION OF THE INVENTION

Within the present invention the term "telmisartan" includes {4'-[2-n-propyl-4-methyl-6-(1-methylbenzimidazol-2-yl)benzimidazol-1-ylmethyl]biphenyl-2-carboxylic acid} in its neutral form as carboxylic acid as disclosed in EP 0 502 314 B1 and U.S. Pat. No. 5,591,762, or in one of its polymorphic forms as disclosed in WO 00/43370, U.S. Pat. No. 6,358,986 and U.S. Pat. No. 6,410,742, or in the form of a pharmaceutically acceptable salt or the solvate, hydrate, or hemihydrate thereof as disclosed in WO 03/037876, including but not limited to the sodium, potassium or ammonium salt. When a salt of telmisartan is used, the sodium salt is preferred. In addition, according to the present invention the term "telmisartan" includes any prodrug, e.g. an ester, which is hydrolyzed in vivo to the pharmacologically active compound.

Within the present invention, the term "vascular headaches" includes any kind of vascular headaches, like migraine, cluster headache, post-traumatic headache, etc. not due to hypertension (i.e. not originated from hypertension). In a preferred embodiment of the invention the term is used for the prevention and/or treatment of migraine.

The term "migraine" is to be interpreted according to: *The Headache Classification Committee of the International Headache Society, Classification and Diagnostic Criteria for Headache Disorders, Cranial Neuralgias and Facial Pain, Cephalalgia* 1988, 8 SUPPL 7, pp. 1-96. It is an often familial symptom complex of periodic attacks of vascular headache, usually temporal and unilateral in onset, commonly associated with irritability, nausea, vomiting, constipation or diarrhoea, and often with photophobia. Attacks are preceded by constriction of the cranial arteries, usually with resultant prodromal sensory (especially ocular) symptoms called Aura, and commence with the vasodilatation that follows.

Migraine can be divided into various specific types including abdominal, acephalic, acute confusional, basilar, classic, common, complicated, fulgurating, Harris', hemiplegic, ocular, ophthalmic and ophthalmoplegic.

The term "cluster headache" is most typically defined as the temporal clustering of attacks during periods usually lasting between 2 weeks and 3 months, separated by intermissions of at least 14 days, but usually several months. This type of cluster headache is also known as "episodic cluster headache". The term "chronic cluster headache" is characterized by the absence of intermissions of at least 14 days for more than one year (*Textbook of Pain*, $3^{rd}$ ed., p. 504,1994).

The term "post-traumatic headache" is headache caused by some head trauma, whereas "tension headache" and "muscular headache" belong to the group of headaches formerly described as "muscle contraction", "psychogenic", "stress" or "essential" (*Textbook of Pain*, $3^{rd}$ ed., p. 504,1994).

With regard to the first aspect of the present invention relating to a method for the prophylaxis of vascular headaches not originating from hypertension, especially migraine, the method comprises the administration of an effective amount of telmisartan to a subject in need of such treatment.

Telmisartan, may be administered orally, bucally, parenterally, nasally, rectally or topically, the oral administration being preferred. Parenteral administration may include subcutaneous, intravenous, intramuscular and intrasternal injections and infusion techniques.

Telmisartan may be administered once, twice or thrice a day in a daily dosage of 10 mg (or 0.143 mg/kg body weight, based on a person of 70 kg) to 500 mg (7.143 mg/kg body weight, based on a person of 70 kg) orally and of about 20 mg (0.286 mg/kg body weight, based on a person of 70 kg) parenterally, preferably of 20 mg (0.286 mg/kg body weight, based on a person of 70 kg) to 100 mg (1.429 mg/kg body weight, based on a person of 70 kg) orally. Particularly preferred is an oral daily dosage of 40 mg (0.571 mg/kg body weight, based on a person of 70 kg) to 80 mg (1.143 mg/kg body weight, based on a person of 70 kg) or specifically of about 80 mg (1.143 mg/kg body weight, based on a person of 70 kg).

Optionally, telmisartan can be administered in combination with other drugs suitable for migraine prophylaxis. Such other drugs are, for example, CGRP antagonists like 1-[$N^2$-[3,5-Dibromo-N-[[4-(3,4-dihydro-2(1H)-oxochinazolin-3-yl)-1-piperidinyl]-carbonyl]-D-tyrosyl]-L-lysyl]-4-(4-pyridinyl)-piperazine,

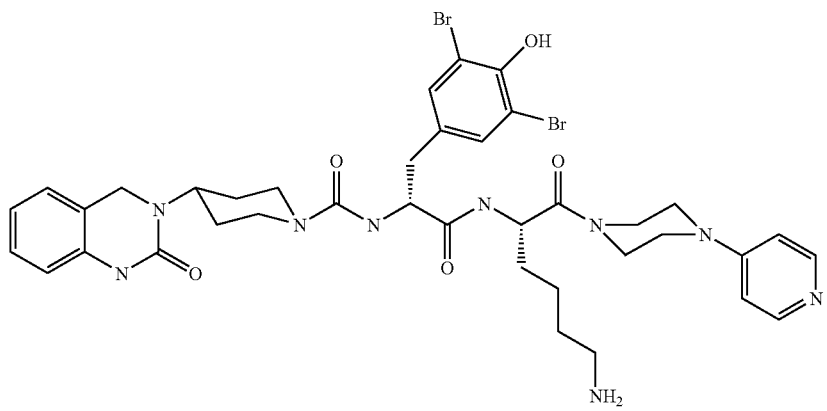 [SMILES: NCCCC[C@H](NC(=O)[C@@H](Cc1cc(Br)c(O)c(Br)c1)NC(=O)N1CCC(N2Cc3ccccc3NC2=O)CC1)C(=O)N1CCN(c2ccncc2)CC1]

and 1-[4-Amino-3,5-dibrom-N-[[4-(2,3,4,5-tetrahydro-2 (1H)-oxo-1,3-benzodiazepin-3-yl)-1-piperidinyl]carbonyl]-D-phenylalanyl]-4-(1-piperidinyl)-piperidin,

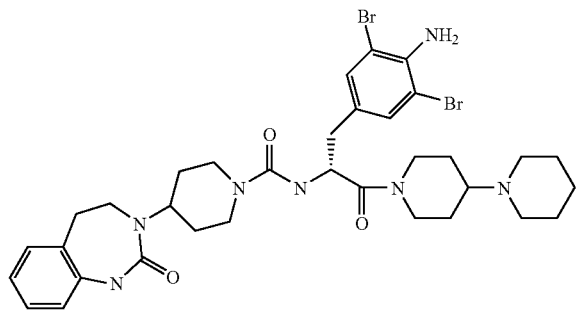 [SMILES: Nc1c(Br)cc(C[C@@H](NC(=O)N2CCC(N3CCc4ccccc4NC3=O)CC2)C(=O)N2CCC(N3CCCCC3)CC2)cc1Br]

which have been disclosed in WO 98/11128, ACE-Inhibitors (e.g. quinapril, captopril, enalapril, ramipril, benazepril, fosinopril, or lisinopril), calcium channel antagonists (e.g. amlodipine, verapamil, diltiazepam, nimodipine, flunarizine, dotarizine, iomerizine HCl, and the like), beta blockers (e.g. atenolol, metropolol, nadolol, propanolol or timolol), alpha 2-agonists (e.g. tizanidine), serotonergic antagonists (e.g. cyproheptadine, pizotifen or methylsergide), anticonvulsants (e.g. divalproex sodium, gabapentin, topiramate, tiagabine, levetiracetam, zonisamide, lamotrigine or valproate), anti-epileptics (e.g. topiramate), antidepressants (e.g. tricyclic like amitriptiline or nortriptyline, selective serotonine reuptake inhibitors, monoamine oxidase inhibitors like pheneizine or other antipsychotics like quentiapine) , $5-HT_{1B-1F}$-agonists (e.g. almotriptan, avitriptan, eletriptan, frovatriptan, naratriptan, rizatriptan, sumatriptan, zolmitriptan), or other AT II type I receptor antagonists (e.g. candesartan, candesartan cilextil, eprosartan, irbesartan, losartan, olmesartan, olmesartan medoxomil, and valsartan) or the corresponding pharmaceutically acceptable salts. Other drugs suitable for migraine prophylaxis are for example magnesium lycinate, riboflavin, botulinum toxin A, montelukast (an anti-inflammatory leukotriene inhibitor), petasites (from petasites hybridus plant, a leukotriene biosynthesis inhibitor), and naproxen.

Preferred compounds to be combined with telmisartan for the prophylaxis of vascular headaches are triptans like almotriptan, avitriptan, eletriptan, frovatriptan, naratriptan, rizatriptan, sumatriptan, zolmitriptan, preferably sumatriptan or zolmitriptan, and CGRP antagonists, preferably 1-[$N^2$-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine as disclosed in WO 98/11128 (page 80, No. 154) and 1-[4-Amino-3,5-dibrom-N-[[4-(2,3,4,5-tetrahydro-2 (1H)-oxo-1,3-benzodiazepin-3-yl)-1-piperidinyl]carbonyl]-D-phenylalanyl]-4-(1-piperidinyl)-piperidin (page 89, No. 231) or their pharmaceutically acceptable salts. The synthesis of these compounds has been disclosed in WO 98/11128 on page 332, example 6, No. 154 for 1-[$N^2$-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine and on page 323, example 4, No. 231 for 1-[4-Amino-3,5-dibrom-N-[[4-(2,3,4,5-tetrahydro-2(1H )-oxo-1,3-benzodiazepin-3-yl)-1-piperidinyl]carbonyl]-D-phenylalanyl]-4-(1-piperidinyl)-piperidin.

A formulation of 1-[$N^2$-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine suitable for powder inhalation has been disclosed in the German patent application DE 102 07 026 A1 and salts thereof like the hydrochloride, sulphate, phosphate, hydrobromide, carbonate, methanesulphonate, p-toluenesulphonate, nitrate, citrate, malate, tartrate, lactate, succinate, gluconate, acetate, formate, propionate, capronate, oxalate, maleate, fumarate, mandelate and hydroxysuccinate, also suitable for powder inhalation have been disclosed in the German patent application DE 102 06 770 A1.

In the acute phase of a migraine attack telmisartan can also be administered in combination with drugs, which are used for acute treatment of migraine as there are anti-inflammatory agents such as NSAID's, cox-2 inhibitors, dopamine agonists like lisurid, antiemetics like dimenhydrinate, β-blockers like timolol or propanolol, antihistamines like buclizine or dimenhydrinate, ergot alkaloids like ergotamine and dihydroergotamine, analgesics like acetaminophen, diclofenac propyphenazon, non-steroidal antiphlogistics like acetylsalicylic acid, naproxen or ibuprofen. Additional drugs which may be administered in the acute phase of a migraine attack include caffeine, iprazochrom, isometheptene, metoclopramide, pangamic acid or the pharmaceutically acceptable salts thereof.

Telmisartan, administered alone or in combination with one or more of the above mentioned drugs can be administered orally, bucally, parenterally, nasally, rectally or topically, the oral administration being preferred. Parenteral administration may include subcutaneous, intravenous, intramuscular and intrasternal injections and infusion techniques.

In combination with one or more of the above mentioned drugs telmisartan may be administered once twice or thrice a day in a daily dosage of 10 mg (or 0.143 mg/kg body weight, based on a person of 70 kg) to 500 mg (7.143 mg/kg body weight, based on a person of 70 kg) orally and of about 20 mg (0.286 mg/kg body weight, based on a person of 70 kg) parenterally, preferably of 20 mg (0.286 mg/kg body weight, based on a person of 70 kg) to 100 mg (1.429 mg/kg body weight, based on a person of 70 kg) orally. Particularly preferred is an oral daily dosage of 40 mg (0.571 mg/kg body weight, based on a person of 70 kg) to 80 mg (1.143 mg/kg body weight, based on a person of 70 kg) or specifically of about 80 mg (1.143 mg/kg body weight, based on a person of 70 kg).

If telmisartan is administered in combination with triptans or a physiologically acceptable salt thereof, the triptans, can be administered by intravenous or subcutaneous route in a dosage of 0.0001 to 1.0 mg/kg of body weight or by oral, rectal, nasal or inhalative route in a dosage of 0.0005 to 10 mg/kg of body weight once, twice or thrice a day.

If telmisartan is administered with sumatriptan or a physiologically acceptable salt thereof sumatriptan may be administered by oral route in a dosage of 0.03 to 1.43 mg/kg of body weight once, twice or thrice a day or by intravenous or subcutaneous route in a dosage of 0.002 to 0.09 mg/kg of body weight once or twice a day or by rectal route in a dosage of 0.007 to 0.36 mg/kg of body weight once or twice a day or by nasal route in a dosage of 0.006 to 0.29 mg/kg of body weight once or twice a day.

If telmisartan is co-administered with zolmitriptan or a physiologically acceptable salt thereof the latter may be administered by oral route in a dosage of 0.0007 to 0.036 mg/kg of body weight once or twice a day.

If telmisartan is administered in combination with CGRP antagonists like 1-[$N^2$-[3,5-Dibromo-N-[[4-(3,4-dihydro-2 (1H)-oxochinazolin-3-yl)-1-piperidinyl]carbonyl]-D-tyrosyl]-L-lysyl]-4-(4-pyridinyl)-piperazine or 1-[4-Amino-3, 5-dibrom-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidin or a physiologically acceptable salt thereof, the CGRP antagonists, preferably 1-[N²-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine and 1-[4-Amino-3,5-dibrom-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidin, may be administered by intravenous or subcutaneous route in a dosage of 0.0001 to 3 mg/kg of body weight or by oral, nasal or inhalative route in a dosage of 0.1 to 20 mg/kg of body weight once, twice or trice a day. For 1-[N²-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine the nasal or inhalative route is preferred and for 1-[4-Amino-3,5-dibrom-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidin oral administration is preferred.

If telmisartan is used in combination with other drugs suitable for prophylaxis and/or acute treatment of migraine, the dosage for the combined migraine drug is appropriately 1/100 of the lowest dose normally recommended up to 1/1 of the normally recommended dosage, preferably 1/50 to 1/6 and more preferably 1/20 to 1/10, orally, bucally, parenterally, nasally, rectally or topically route. The normally recommended dose for the combined migraine drug should be understood to be the dose disclosed in Rote Liste® 2003, Editio Cantor Verlag, Aulendorf or disclosed in Physicians' Desk Reference 2003, 57. Ed.

If the method comprises co-administration of telmisartan and another drug, it is possible to administer a pharmaceutical composition comprising both telmisartan and the other antimigraine drug, or to administer two pharmaceutical compositions, one comprising telmisartan as active ingredient and the other comprising the other antimigraine drug as active ingredient jointly or timely shifted. By the expression "jointly or timely shifted" administration of the telmisartan containing and the other antimigraine drug containing pharmaceutical composition for the purpose of the present invention it is understood that both pharmaceutical compositions are administered to a patient in need thereof simultaneously or in a time interval within one day, however, in some cases it may also be possible to have a better effect, if the telmisartan containing pharmaceutical composition and the antimigraine containing pharmaceutical composition are administered in an interval of more than 24 hours. If the compositions are administered in a time interval, the composition comprising telmisartan can be administered before or after administration of the other antimigraine drug.

With regard to the second object of the present invention, pharmaceutical compositions are provided for the prophylaxis of vascular headaches which do not originate from hypertension, in particular migraine. These compositions comprise a therapeutically effective amount of telmisartan, optionally in combination with at least one other drug suitable for the prophylaxis of migraines, preferably, triptans or CGRP antagonists or pharmaceutically acceptable salts thereof as a combined preparation for simultaneous or sequential administration.

Telmisartan and the other active compounds can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents. Moreover, such oral pharmaceutical formulations can be suitably sweetened and/or flavoured by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages. Other suitable dosage forms for the compounds of this invention include controlled release formulations and devices well known to those who practice in the art.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatine and acacia. Additionally, lubricating agents such as magnesium stearate, sodium lauryl sulfate and talc or compositions of a similar type may also be employed as fillers in soft and hard-filled gelatine capsules; included lactose or milk sugar as well as high molecular weight polyethylene glycols. When aqueous suspensions and/or elixirs are desired for oral administration, the essential active ingredient therein may be combined with various sweetening or flavouring agents, colouring matter or dyes and, if so desired, emulsifying agents and/or water, ethanol, propylene glycol, glycerine and various like combinations thereof.

For purposes of parenteral administration, solutions of the compounds in sesame or peanut oil or in aqueous propylene glycol may be employed, as well as sterile aqueous solutions of the corresponding pharmaceutically acceptable salts. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these injectable solutions to insure that the final products are obtained in a sterile condition.

For purposes of transdermal administration, the dosage form of the particular compound or compounds may include, by way of example, solutions, lotions, ointments, creams, gels, suppositories, rate-limiting sustained release formulations and devices therefore. Such dosage forms comprise the particular compound or compounds and may include ethanol, water, penetration enhancer and inert carriers such as gel-producing materials, mineral oil, emulsifying agents, benzyl alcohol and the like.

A pharmaceutical composition according to the invention may comprise a single dosage unit of 3 to 500 mg, preferably 6 to 100 mg, more preferably 10 to 80 mg telmisartan if orally administered. Particularly preferred is a single dosage unit of 40 or 80 mg of telmisartan for oral administration. For parenteral administration the pharmaceutical composition may comprise a single dosage unit of 6 to 20 mg.

If telmisartan is used in combination with other drugs used for the treatment and/or prevention of migraine, the pharmaceutical composition according to the present invention may comprise a single dosage unit of 1/300 of the lowest dose normally recommended up to 1/1 of the normally recommended dosage, preferably 1/150 to 1/6 and more preferably 1/60 to 1/10 of the combined migraine drug for oral, bucal, parenteral, nasal, rectal or topical administration. The normally recommended dose for the combined migraine drug should be understood to be the dose disclosed in Rote Liste® 2003, Editio Cantor Verlag, Aulendorf or disclosed in Physicians' Desk Reference 2003, 57. Ed.

For example, a pharmaceutical composition according to the invention may comprise a single dosage unit of 40 or 80 mg telmisartan and a single dosage unit of 0.1 to 10 mg of 1-[$N^2$-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine or a single dosage unit of 0.1 to 10 mg of 1-[4-Amino-3,5-dibrom-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidin or a single dosage unit of 1 to 100 mg of sumatriptan or a single dosage unit of 0.1 to 2.5 mg of zolmitriptan.

All doses or dosage units of a physiologically acceptable salt of an active compound mentioned hereinbefore and below should be understood as the dose or dosage of the active compound itself.

Furthermore, if telmisartan is used in combination with another drug used for the treatment and/or prevention of migraine or a physiologically acceptable salt thereof, the pharmaceutical composition according to the invention may be a kit of parts which kit comprises (a) a first containment containing a pharmaceutical composition comprising a therapeutically effective amount of telmisartan or a physiologically acceptable salt thereof and one or more pharmaceutically acceptable diluents and/or carriers; and (b) a second containment containing another drug used for the prophylaxis of migraine or a physiologically acceptable salt thereof and one or more pharmaceutically acceptable diluents and/or carriers.

A preferred kit of parts comprises a triptan like almotriptan, avitriptan, eletriptan, frovatriptan, naratriptan, rizatriptan, sumatriptan, zolmitriptan, or a CGRP antagonists in the second containment.

More preferably a kit of parts comprises sumatriptan, zolmitriptan, 1-[$N^2$-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine or 1-[4-Amino-3,5-dibrom-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidin in the second containment.

With regard to the third object, the present invention provides the use of telmisartan for the manufacture of a pharmaceutical composition for the prophylaxis of vascular headaches which do not originate from hypertension, in particular migraine.

As already mentioned, telmisartan can be used in its neutral form as carboxylic acid, or in one of its polymorphic forms, or in the form of a pharmaceutically acceptable salt or the solvate, hydrate, or hemihydrate thereof, including but not limited to the sodium, potassium or ammonium salt. Additionally, telmisartan can be administered as a prodrug, e.g. an ester, which is hydrolyzed in vivo to the pharmacologically active compound.

Telmisartan can be administered using for instance pharmaceutical formulations sold under the trade name Micardis® or a formulation as disclosed, for example in EP 0 502 314 B1, or WO 03/037876 or using, for example, one of the following pharmaceutical formulations:

tablets containing 20, 40 or 80 mg of active substance, capsules containing 20, 40 or 80 mg of active substance, Furthermore, telmisartan may be used in combination with another drug used for the prophylaxis of migraine, preferably a triptan or a CGRP antagonist or a physiologically acceptable salt thereof for the manufacture of a pharmaceutical composition for the prophylaxis of vascular headaches which do not originate from hypertension, in particular migraine. These drugs and preferred embodiments thereof as well as pharmaceutical compositions are mentioned hereinbefore under the first and second aspect of the invention. Most preferred with respect to all aspects of the invention is the combination of telmisartan with more preferably sumatriptan, zolmitriptan, 1-[$N^2$-[3,5-Dibromo-N-[[4-(3,4-dihydro-2(1H)-oxochinazolin-3-yl)-1-piperidinyl]carbonyl]-D-tyrosyl]-L-lysyl]-4-(4-pyridinyl)-piperazine or 1-[4-Amino-3,5-dibrom-N-[[4-(2,3,4,5-tetrahydro-2(1H)-oxo-1,3-benzodiazepin-3-yl)-1-piperidinyl]carbonyl]-D-phenylalanyl]-4-(1-piperidinyl)-piperidin or of physiologically acceptable salts thereof.

Several of the drugs used for the treatment or prevention of migraine mentioned hereinbefore are already on the market, e.g. acetylsalicylic acid is sold under the trade name Aspirin®, sumatriptan is sold under the trade name imigran®, zolmitriptan is sold under the trade name ascotop®, irbesartan under the trade name Aprovel®, candesartan cilexetil under trade name Atacand®, valsartan under the trade name Diovan®, Iprazochrom under the trade name Divascan®, topiramate under the trade name Topamax® and dihydroergotamin and the pharmaceutically acceptable salts thereof under the trade name Dihytamin®. A combination of acetylisalicylic acid, acetamionophen and caffeine is sold under the trade name Thomapyrin®.

What is claimed is:

1. A method for prophylaxis of vascular headache which does not originate from hypertension, the method comprising co-administering a therapeutically effective amount of telmisartan and a therapeutically effective amount of at least one other drug suitable for the prophylaxis of migraine to a subject in need of such a treatment by oral, rectal, nasal or inhalative administration, wherein the other drug is a triptan.

2. The method according to claim 1, wherein the other drug is a triptan selected from the group consisting of almotriptan, avitriptan, eletriptan, frovatriptan, naratriptan, rizatriptan, sumatriptan, zolmitriptan or a physiologically acceptable salt thereof.

3. The method according to claim 2, wherein the triptan is administered by oral, rectal, nasal or inhalative route in a dosage of 0.0005 to 10 mg/kg of body weight once, twice or trice a day.

4. The method according to claim 1, wherein the telmisartan is administered by oral route in a dosage of 0.143 to 7.143 mg/kg of body weight once, twice or thrice a day.

5. The method according to claim 1, wherein the telmisartan is administered by oral route in a dosage of 0.571 to 1.142 mg/kg body weight once, twice or thrice a day.

6. The method according to claim 1, wherein the vascular headache is a migraine headache.

7. The method according to claim 1, wherein the telmisartan is administered by oral route in a dosage of 0.286 to 1.429 mg/kg body weight once, twice or thrice a day.

* * * * *